United States Patent
Siegrist et al.

(10) Patent No.: US 11,073,486 B2
(45) Date of Patent: Jul. 27, 2021

(54) X-RAY DETECTOR DEVICE AND DEVICE FOR THE X-RAY INSPECTION OF PRODUCTS, IN PARTICULAR FOODSTUFFS

(71) Applicant: Wipotec GmbH, Kaiserslautern (DE)

(72) Inventors: Michael Siegrist, Kaiserslautern (DE); Ulrich Heil, Glan-Münchweiler (DE); Christian Bur, Saarbrücken (DE); Kai Hoffmann, Weidenthal (DE)

(73) Assignee: Wipotec GmbH, Kaiserslautern (DE)

( * ) Notice: Subject to any disclaimer, the term of this patent is extended or adjusted under 35 U.S.C. 154(b) by 0 days.

(21) Appl. No.: 16/858,853

(22) Filed: Apr. 27, 2020

(65) Prior Publication Data
US 2020/0363347 A1 Nov. 19, 2020

(30) Foreign Application Priority Data

May 3, 2019 (DE) .......................... 102019111463.2

(51) Int. Cl.
*G01N 23/083* (2018.01)
(52) U.S. Cl.
CPC ... *G01N 23/083* (2013.01); *G01N 2223/1016* (2013.01); *G01N 2223/618* (2013.01)
(58) Field of Classification Search
None
See application file for complete search history.

(56) References Cited

U.S. PATENT DOCUMENTS

| 2009/0074132 A1 | 3/2009 | Schlomka et al. |
| 2009/0168958 A1* | 7/2009 | Cozzini ............... G01V 5/0025 378/57 |
| 2010/0012845 A1 | 1/2010 | Baeumer |
| 2012/0145910 A1 | 6/2012 | Suyama |

(Continued)

FOREIGN PATENT DOCUMENTS

| EP | 3287774 A1 | 2/2018 |
| JP | 2008-518226 A | 5/2008 |
| JP | 2011-64640 A | 3/2011 |

(Continued)

OTHER PUBLICATIONS

Japan patent application 2020-077275 Office Action dated May 21, 2021.

*Primary Examiner* — Hoon K Song
(74) *Attorney, Agent, or Firm* — The Culbertson Group, P.C.

(57) ABSTRACT

An X-ray detector device for a device for the X-ray inspection of products includes a first line detector with a first discrete spatial resolution, a second line detector with the same or lesser second discrete spatial resolution, and an evaluation and control unit. The first line detector is operable to capture X-radiation in a non-spectrally resolved fashion along a first capture line transverse to a product movement direction to generate first image data. The second line detector is operable to capture the X-radiation in a spectrally resolved fashion along a second capture line parallel to the first capture line to generate second image data. The evalu- (Continued)

ation and control unit is operable to evaluate the first and second image data to detect at least one predefined feature of the product with the first discrete spatial resolution by combining the items of information contained in the first and second image data.

16 Claims, 4 Drawing Sheets

(56) References Cited

U.S. PATENT DOCUMENTS

2013/0079918 A1  3/2013  Spencer et al.
2020/0378907 A1* 12/2020  Morton .................. G06T 7/187

FOREIGN PATENT DOCUMENTS

| | | |
|---|---|---|
| JP | 2012-528397 A | 11/2012 |
| JP | 2016-29367 A | 3/2016 |
| WO | 2018102051 A1 | 6/2018 |

* cited by examiner

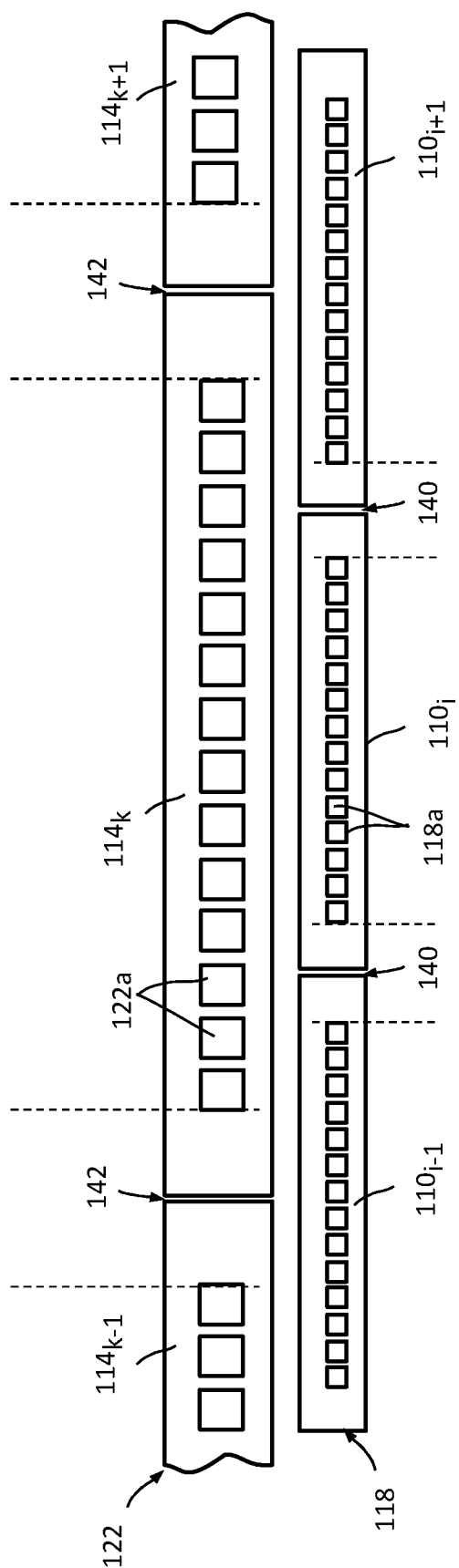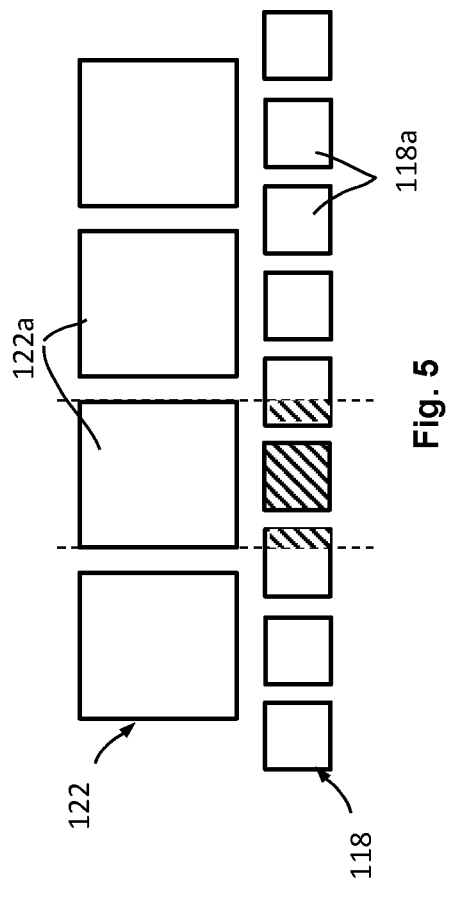

US 11,073,486 B2

X-RAY DETECTOR DEVICE AND DEVICE FOR THE X-RAY INSPECTION OF PRODUCTS, IN PARTICULAR FOODSTUFFS

TECHNICAL FIELD OF THE INVENTION

The invention relates to X-ray detector devices for use in X-ray inspection systems for the inspection of products, in particular foodstuffs. The invention also relates to X-ray inspection devices which employ such an X-ray detector device.

BACKGROUND OF THE INVENTION

Line detectors, which are provided transverse to the movement direction of the products to be examined, are usually used for the X-ray inspection of moving products. Instead of the product moving, the entire X-ray inspection device or at least the relevant X-ray detector device can also be moved relative to the product to be examined. The product to be examined is scanned by means of the line detector, which detects the X-radiation generated by one or more X-ray sources, and the image data generated line by line are converted to an image of the product to be examined. To generate the image, the image data can be processed in a suitable manner. The thus-generated image can be inspected by image processing. In particular, the image of the product to be examined can be inspected for whether one or more predefined features are present or achieved. For example, a foodstuff such a piece of meat can be examined for whether there are undesired foreign bodies in it, such as bone fragments, metal swarf from processing machines, glass splinters, plastics, stones or the like.

For this purpose, it is known to use spectrally integrating line detectors (non-spectral detectors) which detect virtually the entire width of the X-ray spectrum of the X-radiation which is generated by the relevant X-ray source. Such line detectors have a comparatively high spatial resolution in the region of for example 0.2 mm over a total detector width of from, for example, 200 to 800 mm or more. The line detectors can be constructed in the form of modules, which can be coupled together with in each case only very small gaps of only a few pixels (for example one to two pixels per module edge) until a desired scan width is achieved. Even very small foreign bodies or contaminations are thus detectable with such non-spectral detectors. This type of detector moreover requires no cooling and is cost-effective to produce.

However, as a result of the spectral integration such non-spectral detectors generate only grayscale values. A grayscale value is dependent on the attenuation of the X-radiation when it passes through the product to be examined. The attenuation is in turn dependent on the thickness of the product and on the material properties.

Thus a non-spectral detector is suitable in particular for detecting extremely small, strongly absorbing foreign bodies, for example metal splinters.

An improvement in the contrast of the image generated by line detectors can be achieved through the dual energy method. There, two non-spectral line detectors are used, the scan images of which are superimposed. The line detectors capture different spectral ranges of the X-radiation that has passed through the product. This is achieved through the use of at least one X-ray filter, which is arranged in front of one of the non-spectral detectors in the beam path. However, such filters operate only as high-pass filters and moreover cannot be produced sufficiently flexibly with respect to the desired filter edge. In addition, they also attenuate the X-radiation to be detected in the desired spectral range. Through the separate capture of different spectral ranges a different item of information is contained in the image signals of the respective line detectors. A total image which has a better contrast than a single-energy image with respect to the recognizability of particular foreign body materials can be generated through a weighted superimposition (for example correctly signed addition of the weighted image data). With a fixed X-ray filter, however, the contrast can only be improved for one or more particular materials. Dual energy methods are therefore not very flexible with respect to their use, as the X-ray filter must be chosen suitably, depending on the application case.

Moreover, the spectral ranges of the X-radiation which are captured by the two non-spectral line detectors usually overlap, with the result that a portion of the same item of information is contained in each of the two image signals. An optimum contrast improvement thus cannot be achieved.

However, the dual energy method makes it possible to remove product regions of a product consisting of only two materials when the two image signals are combined suitably. Thus, for example, the contrast in the region of a foreign body, i.e. of a first material, inside the product, i.e. a second material, can be optimized. However, this only applies to a substantially homogeneous product made of a single material (or a combination of materials with very similar attenuation properties for the X-radiation), in which foreign bodies made of a further material (with different attenuation properties for the X-radiation) are contained.

Furthermore, in recent years spectrally resolving line detectors have been developed which can likewise be coupled modularly. However, such spectral line detectors, which make sufficiently large scan widths of from 200 to 800 mm or more possible, are currently only available with a relatively coarse spatial resolution, i.e. with a relatively large pixel pitch, of for example 0.8 mm. Such spectral line detectors are capable of capturing the entire spectral width of the X-radiation to be detected, for example in the range of from 20 keV to 160 keV. These detectors provide a large number of energy channels, for example up to 256, for the spectral resolution. Such a spectral line detector therefore makes it possible to generate a number of partial images corresponding to the number of energy channels. The information contained in the partial images in each case can be used and processed in many ways. In particular, this information makes it possible to recognize materials or material combinations as well as to detect layer thicknesses.

In addition to the disadvantage of a relatively coarse spatial resolution, such spectral line detectors are expensive and have a larger overall size as compared to simple non-spectrally resolving line detectors. Moreover, much more energy is needed to operate spectral line detectors than to operate non-spectral detectors, wherein the high energy consumption makes a complex cooling necessary.

A further substantial disadvantage of the spectral line detectors is the long start-up time, which can be in the region of 30 minutes. This long start-up time is conditional on the fact that the spectral line detector does not guarantee a sufficient charge separation until after a certain time.

SUMMARY OF THE INVENTION

It is an object of the invention to provide an X-ray detector device for a device for the X-ray inspection of products, in particular foodstuffs, which is cost-effective to produce and makes possible an improved recognition of foreign bodies in a product to be examined. A further object of the invention is to provide an X-ray inspection device with such an X-ray detector device.

An X-ray detector device according to one aspect of the invention has at least one first line detector with a first, more discrete spatial resolution (i.e. a larger number of pixels per unit of length), which is designed to capture broad-band X-radiation along one or more parallel first capture lines transverse to a movement direction of a relative movement between a product to be examined and the X-ray detector device. This first line detector detects the X-radiation that has passed through the product to be examined non-spectrally resolved over a predefined capture width and generates first image data, wherein the first image data comprise one grayscale value for each discrete location along the respective first capture line.

At this point it may be mentioned that the term "X-radiation" in the present description and claims comprises any type of high-energy electromagnetic radiation, in particular X-radiation in the range above 100 eV, in particular above 1 keV, as well as terahertz radiation, i.e. radiation in the range of from approx. 0.3 THz to 30 THz.

Instead of a single such non-spectrally resolving line detector with higher spatial resolution, i.e. a small pixel pitch, two or more such line detectors, which are designed in a manner known per se to generate a dual energy image, can also be used, wherein at least one of these line detectors has a filter for filtering the X-radiation to be detected. Instead of a filter, a further X-ray source, which has different spectral characteristics from a first X-ray source, in particular has the maximum of the spectrum at a different energy value, can also be used in a corresponding X-ray inspection device with such an X-ray detector device. It is noted here that the term "multiple energy" may be used in this disclosure and the accompanying claims to imaging techniques which utilize two bands of the X-radiation spectrum ("dual energy") or more than two such bands.

The X-ray detector device according to this aspect of the invention furthermore has at least one second line detector with a second discrete spatial resolution, which is smaller than or equal to the first discrete spatial resolution, which detects the X-radiation along one or more parallel second capture lines which run parallel to the first capture lines discretely spectrally resolved over the predefined capture width and generates second image data. The respective second line detector assigns the X-ray quanta for the spectral resolution depending on their energy, to a large number of energy channels, and the second image data for each discrete location along the respective second capture line comprise one spectral value for each energy channel.

Each of the line detectors can also have several lines. Thus, several image lines of a product to be scanned can be recorded and read at the same time. The several lines can also be used to implement the Time Delay Integration method (TDI method) in order to improve the signal-to-noise ratio.

The image signals of all line detectors are fed to an evaluation and control unit, which is also designed, among other things, to evaluate the first and second image data such that at least one predefined feature of the product to be examined is detected with the first discrete spatial resolution by combining the items of information contained in the first and second image data. The evaluation and control unit can be designed as a combination of hardware and software, and in particular can comprise an image processing unit with a sufficiently rapid image processor. From the image data of the line detectors, the image processing unit generates one or more images and analyzes the images with respect to at least one predefined feature. The evaluation and control unit or the image processing unit uses information which the second, i.e. the spectrally resolving, line detector provides, in order to generate the total image to be analyzed and/or to analyze a generated total image. In this way, the advantages of the spectrally resolving line detector can be utilized for the generation of a total image and/or for the analysis of a total image in which the information of the image data provided by the at least one first, non-spectrally resolving line detector at least is also contained.

This advantage can in particular also be utilized when the second discrete spatial resolution of the at least one non-spectrally resolving line detector is much lower than the first discrete spatial resolution of the at least one spectrally resolving line detector.

The at least one predefined feature for which the evaluation and control unit examines a previously generated total image can be the position of a foreign body inside the product, the material of the foreign body, the thickness of the product, the material of the product, the thickness of material layers of the product, or the position of overlap regions of several products.

According to some embodiments of the invention, the line detectors are provided in a common housing. Instead of a housing, the line detectors can of course also be arranged on any, not closed, carrier in a fixed position relative to each other. The line detectors (with or without housing; with or without carrier) can also be provided in a common radiation protection housing. A device for the X-ray inspection of moving products can hereby be realized in a simple and also cost-effective manner, in particular as concerns the radiation protection.

According to some embodiments of the invention, the evaluation and control unit actuates the at least one first and the second line detector such that a synchronous capture of the image data on the first and second capture lines is effected depending on the speed of the relative movement between the product to be examined and the X-ray detector device, in order to obtain, on the first and second capture lines, in each case line image data which correspond substantially to the same beam path through the product to be examined. In the case of such a synchronized generation of the image data by the individual line detectors, a total image can be generated with less effort, as at the most an adaptation, e.g. interpolation of the image data (e.g. of only one line detector), in the direction of the capture lines is necessary here. On the contrary, the image data from the lines of the line detectors can be directly combined, e.g. added together weighted. For this purpose, the movement speed must be sufficiently precisely known, likewise the distance between the line detectors in the movement direction.

According to additional embodiments, the evaluation and control unit actuates the at least one first and the second line detector such that an asynchronous data capture on the first and second capture lines is effected, wherein line image data are captured on the first and second capture lines in each case at a line-scanning rate which is preferably equal to or greater than the dimension of the pixels of the respective line detector in the direction of the relative movement divided by the speed of the relative movement. The product to be examined can thus be scanned without gaps (viewed in the movement direction). In the case of the generation of a total image from the image data of several line detectors, an adaptation of the image data, for example by interpolation, also viewed in the movement direction, may be carried out here as required.

It may be noted at this point that, in the case of the generation of a total image from the image data of two or more line detectors, the evaluation and control unit or the image processing unit can apply any necessary operation in order to correct the distances between the line detectors, the different pixel pitch thereof, angle errors between the line detectors, a different distance of the line detectors from the X-ray source and the like. In particular a (linear or non-linear) interpolation, a geometric transformation (to correct angle errors in the case of non-parallel capture lines) and a weighting of the image data (e.g. in the case of different detector sensitivities) come into consideration as necessary operations.

In the case of the asynchronous capture of the image data of the at least one first, non-spectral line detector and of the second, spectral line detector, the evaluation and control unit can be designed such that the image data are passed to the image processing unit as a single data stream. This is suitable in particular if the evaluation and control unit is designed decentralized and the image processing unit is further away from a data capture unit to which the image data of the individual line detectors are fed as single data streams. For this purpose, the data capture unit can provide the image data with time information which includes the capture times in absolute form or relative to a reference point. For example, each image line in the common image data stream can be assigned one item of time information. The image data from image lines of the different line detectors can likewise be suitably characterized in the data stream as originating from a particular line detector. Such a data transfer can of course also be used in the case of a synchronous scanning.

As already explained briefly above, the evaluation and control unit can create a total image from the image data of the at least one first line detector and of the second line detector, in particular by interpolation and/or geometric transformation of the image data of the at least one second line detector and/or the image data of the at least one first line detector. The total image thus includes information from the two different types of line detector.

According to further embodiments of the invention, the at least one first line detector and the second line detector comprise, in the direction of the relevant capture line, several similar modules strung together at butt joints, wherein the butt joints of the at least one first line detector and the butt joints of the second line detector are offset relative to each other. The blind spots of one line detector can thus be at least partially compensated for by the image data of the respectively other line detector. However, in many cases the second line detector cannot provide the higher spatial resolution of the first line detector and the first line detector cannot provide the spectral resolution of the second line detector. However, this disadvantage is acceptable in particular for the embodiments explained below, in which the image data of the second line detector are used in order to generate partial image data which have a freely selectable spectrum, and these partial image data are combined with the image data of the first line detector to form a dual energy total image, or in which the image data of the second line detector are used in order to obtain information relating to overlap regions or the product thickness, which is then used to ascertain variable threshold values for evaluating a total image.

These modular line detector embodiments make a small design possible, as the modules are arranged in a straight line and the modules of the second, spectrally resolving line detector, which have a larger design because of the heat sinks, can be arranged close to the modules of the at least one first, non-spectrally resolving line detector, which have a smaller design. If such blind spots are to be prevented, then only an imbricated arrangement of the modules would come into consideration, which would, however, result in a significantly enlarged design.

According to further variants of the invention, the evaluation and control unit can weight, for each discrete location, the spectral values of the energy channels of the image data of the second line detector, in particular multiply them by in each case one factor, and add the weighted spectral values together to form a total spectral value. In this way, the evaluation and control unit can generate dual energy image data or multiple energy image data from the first image data of the at least one first line detector and the second image data, processed in such a way, of the second line detector. The evaluation and control unit or the image processing unit can freely select the spectrum of the thus-processed second image data through any desired weighting (a weighting with the factor zero corresponds to a sharp delimitation of a corresponding spectral range) and thus generate a dual energy image which is adapted for the recognition of quite particular features of the product to be examined. For example, the spectrum of the processed second image data can be adapted for the recognition of foreign bodies made of a particular material.

The weighting can be effected for example such that a particular spectral range, e.g. the energy channels from 20 to 40 keV, is weighted with the factor 1 and all other energy channels are removed through a zero weighting. It was not possible to generate such a sharply delimited spectrum in a lower energy range with a filter for the X-radiation, as these filters for one thing are available only as high-pass filters and for another have a small edge steepness.

In this way, the invention thus makes a dual energy method possible in which the line detector with usually higher spatial resolution detects the spectrum of the X-radiation as a whole and the line detector with usually lower spatial resolution provides any desired and flexibly selectable spectrum. This spectrum can moreover be selected as desired after the spectrally resolved capture of the X-radiation.

This principle can also be realized in that the spectrally resolving line detector for its part carries out a preprocessing. For example, the spectral line detector can only read selected energy channels in the form of the image data signal, which corresponds to a weighting of the unread energy channels with the factor zero. Then the evaluation and control unit can again perform the weighting of the read energy channels and the determination of a total spectral value corresponding to a predetermined weighting profile.

The spectrally resolving line detector can also be designed such that not only are particular energy channels read (individually), but the line detector at the same time performs an adding-up of the spectral values of the individual channels to form a total spectral value. The total spectral value can then be weighted by the evaluation and control unit (with a single factor). For this purpose, the spectrally resolving line detector can also be designed such that the spectral width of the energy channels is adjustable. In this way, it is possible (by manual input or an input by the evaluation and control unit) to actuate the spectrally resolving sensor such that it provides a spectral value for an adjustable spectral range, for example a spectral range of from 20 keV to 40 keV. This spectral value can then be weighted directly by the evaluation and control unit and used to generate a dual energy image.

It may be noted at this point that the evaluation and control unit, through the use of a weighting profile which has one weighting factor for each energy channel, can perform (pixel by pixel) a weighting, which can be selected as desired, of the spectrum provided by the spectrally resolving sensor. The weighting can at the same time effect a selection of an energy channel if the respective weighting factor is not equal to zero, and an actual weighting of the spectral value of the relevant energy channel with the respective weighting factor. If the weighting factors are constant for adjacent energy channels which are used to generate partial image data for a dual energy image, the spectral values of these energy channels can also only be added together to form a total spectral value before the total spectral value with the (constant) weighting factor is used to generate the dual energy image.

According to embodiments of the invention, items of information can be stored in the evaluation and control unit, or the evaluation and control unit can have access to items of information, which are weightings of energy channels preferably suitable for the detection of one or more particular predefined features of the product to be examined. In particular, these items of information can be present in the form of weighting profiles, wherein a weighting profile can assign an (in principle freely selectable) weighting factor to each energy channel. Each weighting profile can be assigned a particular feature which is advantageously detectable, in particular with good contrast, using the dual energy total image generated with this profile. For example, foreign bodies made of a particular plastic, e.g. of polyethylene, can be detected with good contrast with one particular weighting profile, while another weighting profile is particularly suitable for the detection of bone fragments in the relevant total image.

The evaluation and control unit can also evaluate the image data of the at least one first line detector and the image data of the second line detector multiple times for a particular product to be examined, in particular for the detection of different predefined features, wherein for each evaluation in each case dual energy image data or multiple energy image data or in each case a corresponding total image are generated using another weighting or another weighting profile for the spectral values of the energy channels of the image data of the second line detector. Different types of evaluations can thus be performed through a single scan of the product. For example, a total image which was generated using a first weighting profile can be examined for the presence of foreign bodies made of metal, and a total image which was generated using a second weighting profile can be examined for the presence of foreign bodies made of plastic.

According to further embodiments, the evaluation and control unit can evaluate the image data of the second line detector for the recognition of product regions with different layer thicknesses and/or regions of overlapping products and identify such regions in the image data of the at least one first line detector or in combined image data. For the inspection of the thus-identified regions, the evaluation and control unit can use a threshold value which is set depending on the grayscale values of one or more of these regions in the relevant total image. For example, the average grayscale value of such a local region in the total image can be ascertained and the threshold value from which the evaluation and control unit recognizes a foreign body can be determined depending on this grayscale value according to a predefined rule. Such a dynamic threshold value provides the advantage of a recognition of foreign bodies or other features of a product to be examined which is correct independent of the thickness of the product or independent of overlapping product regions.

The thickness of a known material can be established through a suitable evaluation of the image data of the second, spectrally resolving line detector. Furthermore, through a suitable evaluation of these data it can even be established which material or which material combination it is. This is because every material generates a characteristic progression of the energy spectrum when an X-ray spectrum which has a sufficient spectral width of e.g. from 20 to 160 keV is transmitted through it. Thus, the progression of the attenuation of the X-radiation that is characteristic of the relevant (at first unknown) material can be determined pixel by pixel as a function of the energy through a comparison of the energy spectrum which was detected without a product and the energy spectrum which was detected with a product. The material can be determined through a comparison of this characteristic progression with known characteristic progressions for respective materials. For this purpose, the evaluation and control unit can compare each detected energy spectrum with stored characteristic progressions of products, for example through a correlation analysis.

While the progression of a detected energy spectrum is indicative of the material, the thickness of the product and also differences in thickness depending on the location can be determined from the attenuation of the detected radiation (in one energy channel or several or all integrated energy channels) if the respective material is known. In this way, overlap regions of two or more products can also be determined. For this purpose, the evaluation and control unit can access items of information which include the relationship between the attenuation and the thickness of the relevant material. These can be values for the energy-dependent absorption coefficient $\mu(E)$, wherein E denotes the energy of the X-radiation. The thickness of a known material can thus be ascertained using the Beer-Lambert law.

According to further embodiments of the invention, to monitor the state of a selected line detector the evaluation and control unit ascertains image data of the line detector to be monitored and image data of a line detector selected as reference line detector, preferably in each case without the presence of a product, wherein to ascertain the image data of the second line detector the evaluation and control unit adds up the spectral values of one, several or all energy channels, and wherein the evaluation and control unit compares the image data of the line detector to be monitored with image data of the reference line detector and generates a "not-ready signal" if inadmissible deviations of the image data of the line detector to be monitored from the image data of the reference line detector are established.

The selection of the energy channels, the spectral values of which are added together to form a total spectral value, can be made such that the same progression of the spectral sensitivity results for both line detectors. If it is known for example that a non-spectrally resolving line detector to be monitored has a sensitivity in the range of from 20 keV to 80 keV and the spectrally resolving line detector (i.e. the reference line detector) has a sensitivity of from 20 keV to 160 keV, only those energy channels of the spectrally resolving line detector which cover the sensitivity range of the non-spectrally resolving line detector, thus the energy channels in the range of from 20 keV to 80 keV, will be used for ascertaining the relevant total spectral value. This procedure is of course independent of whether the spectrally resolving line detector acts as reference line detector or represents the line detector to be monitored. Instead of an addition of the spectral values of the relevant energy channels by the evaluation and control unit, the spectrally resolving sensor itself can provide this functionality. In particular, it can provide only the selected energy channels in the image data signal or already transmit the total spectral value to the evaluation and control unit in the image data signal.

In addition, it is possible to take into account a known spectral sensitivity progression of a non-spectrally resolving line detector (within the spectral width of the energy channels of the spectrally resolving line detector that are to operate). For this purpose, the evaluation and control unit can weight the spectral values that are to operate of the respective energy channels suitably before the addition. In this way, the spectral sensitivity of the spectrally resolving line detector can be brought closer to the spectral sensitivity of a non-spectrally resolving line detector.

By applying this monitoring method, in particular the readiness of the second, spectrally resolving line detector can be checked and it can be established if the latter is switched on. This is because, as explained above, it can take a longer time, e.g. 30 min, for the spectrally resolving sensor to achieve a sufficient charge separation. For this purpose, the grayscale value of a non-spectrally resolving sensor can be compared pixel by pixel with the corresponding grayscale value of the spectrally resolving sensor, wherein the grayscale value of the spectrally resolving sensor results from adding up the spectral values of all energy channels (for each pixel). If the evaluation and control unit knows the ratio of the pixel grayscale values, corresponding to each other, of the two sensors at full (correct) operational capability, it can generate the "not-ready signal" if the grayscale value of a comparison pixel of the non-spectrally resolving line detector deviates by more than an admissible value from the grayscale value of the corresponding comparison pixel of the spectrally resolving line detector.

The "not-ready signal" can already be generated when an inadmissible deviation is established for a single pair of comparison pixels corresponding to each other. It may be pointed out that a "not-ready signal" can be generated in all cases where the image data of the line detector to be monitored deviate by more than a predefined value from the image data of the reference line detector.

The evaluation and control unit can carry out this pixel-by-pixel comparison, using comparison pixels corresponding to each other. A comparison pixel can consist of one or more pixels of a line detector that are to be taken into account entirely or proportionately. The comparison pixels are chosen such that two comparison pixels corresponding to each other cover the same distance on the respective capture lines, i.e. the width of each pair of comparison pixels corresponding to each other is identical, wherein the distance which is covered by a comparison pixel on the relevant capture line arises through a parallel shift of the distance which the respectively corresponding comparison pixel covers on the relevant other capture line. For the determination of the grayscale value of a comparison pixel, the values of all pixels which lie entirely or partially within the width of the comparison pixel are added up, wherein the grayscale value of a pixel which does not lie with its entire width within the width of the respective comparison pixel is weighted with the ratio with which the relevant pixel lies with its width within the width of the comparison pixel.

If, for example, the wider pixels of the second line detector with lower spatial resolution are in each case used as comparison pixels, and if in each case a narrower pixel of the first line detector with higher spatial resolution lies entirely within the width of the comparison pixel of the second line detector and two pixels of the first line detector with higher spatial resolution lie with half their width within it, the grayscale value of the corresponding comparison pixel of the first line detector, which consists of the entire pixel and the two half pixels of the first line detector, is determined through the addition of the grayscale value of the entire pixel and the grayscale values, weighted with a factor of 0.5, of the half pixels in each case.

In this way, a simple comparison of the image data signals of the line detector determined as reference line detector and of the line detector to be monitored can be effected.

A device according to the invention for the X-ray inspection of products, in particular foodstuffs, has a radiation-generating device with at least one X-ray source for generating X-radiation with a predefined spectral width and is designed to transmit the generated X-radiation through a product to be examined that is moving in a movement direction with a predefined movement speed. Furthermore, the device has an X-ray detector device according to the invention, such as was described above.

According to some embodiments, the at least one first line detector and the second line detector are arranged such that the one or more second capture lines of the second line detector do not lie in the shadow of the at least one first line detector and the one or more first capture lines of the first line detector do not lie in the shadow of the second line detector, and that the one or more first and second capture lines have as small as possible a distance between them in the movement direction of the product to be examined. A scanning of product regions by the at least two line detectors which, viewed in the movement direction, have as small as possible a distance between them hereby results. Variations in the movement speed which are not known to the evaluation and control unit therefore have a small influence on the generation of a total image, as the identical product region is irradiated and scanned at only a very short time interval. Moreover, the beam path runs on approximately the same path through the product and a small dimension of the detector device results.

The at least one first line detector and the second line detector, viewed in the radiation direction, can be arranged overlapping, wherein the one or more first and second capture lines have a different distance from the at least one X-ray source, which is preferably chosen as small as possible, depending on the overall size of the at least one first and the second line detector. A very small overall height is thus achieved.

These and other advantages and features of the invention will be apparent from the following description of representative embodiments, considered along with the accompanying drawings.

BRIEF DESCRIPTION OF THE DRAWINGS

FIG. 4 is a section of a schematic top view of the two lines of a further embodiment of an X-ray detector device similar to the embodiment in FIGS. 2 and 3.

FIG. 5 is a schematic section of a variant of the embodiment in FIG. 5.

DESCRIPTION OF REPRESENTATIVE EMBODIMENTS

Figure 1:
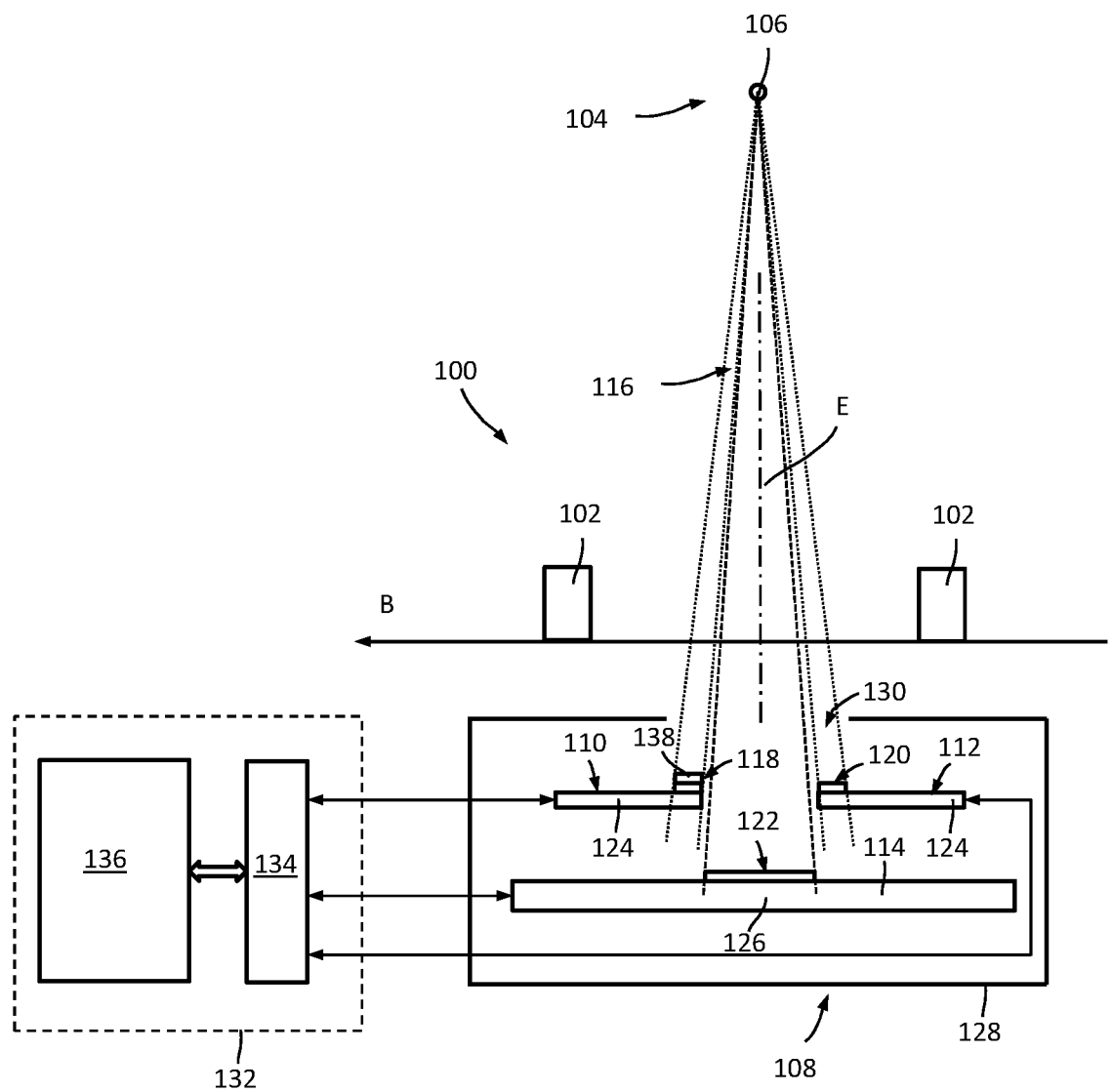
FIG. 1 is a schematic representation of a first embodiment of a device for the inspection of products with a first embodiment of an X-ray detector device with two non-spectrally resolving line detectors and one spectrally resolving line detector.

FIG. 1 shows a schematic representation of a first embodiment of a device 100 for the X-ray inspection of products 102, in particular foodstuffs, with a radiation-generating device 104 with at least one X-ray source 106 and with an X-ray detector device 108 with two non-spectrally resolving line detectors 110, 112 and one spectrally resolving line detector 114.

The X-ray source 106 generates a fan-shaped X-ray beam 116, which has a center plane E which is perpendicular to a movement direction B, in which the products 102 to be examined are moved through the X-ray beam 116. In the plane E, the X-ray beam 116 has an angle which is designed such that the X-ray beam 116 is transmitted through the product 102 to be examined in its entire width (extending perpendicular to the plane of the drawing). A conveying device (not represented), for example a conveyor belt, can be provided to move the product 102.

The non-spectrally resolving line detectors 110, 112 have in each case a single line 118, 120 of pixels, which detects the X-radiation of the X-ray beam 116 along a capture line in each case. In this connection, a capture line is referred to, even if the pixels of the respective line 118, 120 have a finite extent. The non-spectrally resolving line detectors 110, 112 have a higher discrete spatial resolution than the spectrally resolving line detector 114, which likewise comprises a line 122 of pixels, which detects the X-radiation of the X-ray beam 116 along a capture line. The discrete spatial resolution of the line detectors 110, 112, i.e. the number of pixels per unit of length or the pixel pitch, can be for example 0.2 mm, and thus four times as large as the pixel pitch of the line detector 114, which can be for example 0.8 mm.

The non-spectrally resolving line detectors 110, 112 face each other with their detector lines 118, 120, which are in each case provided on one edge of a carrier 124, wherein, viewed in movement direction B, a distance remains between the detector lines 118, 120. This distance corresponds approximately to the width of the detector line 122 of the spectrally resolving line detector 114. The detector line 122 is provided approximately in the middle on a carrier 126, which can also carry heat sinks and other components. The heat sinks can also form the carrier 126. The detector lines 118, 120 can, as represented in FIG. 1, have the same distance from the X-ray source 106. The spectrally resolving line detector 114, which as a result of the necessary heat sinks has a larger design than the non-spectrally resolving line detectors 110, 112, is located, viewed in the direction of the X-ray beam 116, underneath the line detectors 110, 112. As the X-radiation which is detected by the line detectors 110, 112 and 114 is to be transmitted through the product 102 as much as possible on the same beam path, it is advantageous to arrange the detector lines 118, 120 and 122 at as small as possible a distance, viewed in the movement direction B, or within as small as possible an angle of the X-ray beam 116 in a plane which is not perpendicular to the center plane of the fan-shaped X-ray beam 116.

The line detectors 110, 112, 114 can, as shown in FIG. 1, be provided in a common housing 128, which can be designed as a radiation protection housing. On its upper side, i.e. the side facing the X-ray source 106, the housing 128 has an opening 130 which makes it possible for the X-ray beam 116 to penetrate into the housing in the direction of the pixel lines 118, 120, 122 of the line detectors 110, 112, 114.

Two or more spectrally resolving line detectors can also be provided instead of a single spectrally resolving line detector 114. This can be advantageous when the non-spectrally resolving line detectors are designed in each case to capture a different maximum spectral width. For example, one of the spectrally resolving line detectors can have a spectral width of from at most 20 keV to 160 keV with a spectral resolution of 256 energy channels and a further spectrally resolving line detector can have a spectral width of from at most 20 keV to 80 keV, likewise with a resolution of 256 energy channels. The further spectrally resolving line detector thus has a spectral resolution that is twice as high as that of the first spectrally resolving line detector.

The line detectors 110, 112, 114 in each case generate an image data signal, which is fed to an evaluation and control unit 132. The evaluation and control unit 132 can have a data capture unit 134 and an image processing unit 136. The image data signals of the line detectors 110, 112, 114 are fed to the data capture unit 134. The image data signals can be combined by the data capture unit 134 to form a single signal or image data stream, which is fed to the image processing unit 136. The image processing unit 136 is designed for the further processing and analysis of the image data. The data capture unit 134 can also be designed such that it actuates the line detectors 110, 112, 114 suitably, in particular with respect to the scanning time points. For this purpose, the data capture unit 134 can feed a clock signal to each of the line detectors, wherein the image data capture by the line detectors can then be effected synchronized with the clock signal.

In the framework of a synchronous image data capture it can in particular be achieved that the non-spectrally resolving line detectors 110, 112, depending on the movement speed of the product 102 to be examined, detect X-radiation which has penetrated the product to be examined substantially on the same path, although temporally offset. Through an arrangement of the line detectors 110, 112 such that the detector lines 118, 120 have as small as possible a distance between them, changes in speed not known to the control and evaluation unit 132 do not have a disadvantageous effect on the synchronicity of the data capture. Naturally, the same is also true for a synchronized scanning of a product 102 by means of the spectrally resolving line detector 114.

The image processing unit 136 can process the image data captured by the line detectors 110, 112, 114 in the following manner. In the embodiment represented in FIG. 1, the image data of the non-spectrally resolving line detectors 110, 112 can be evaluated corresponding to a dual energy method known per se. For this purpose, the line detector 110 can have an X-ray filter 138, which is provided in the course of the beam path between the X-ray source 106 and the detector line 118. By means of the non-spectrally resolving line detectors 110, 112, in each case image data can hereby be captured which in each case have a grayscale value which results from integration of the entire detected X-ray spectrum in each case, depending on the intensity of the detected X-radiation. As known per se, in such an embodiment a higher contrast can be achieved in the detection of foreign bodies in a product 102 if the foreign bodies consist of a material which has a different absorption coefficient from the product itself.

However, the image data of the spectrally resolving line detector 114 provide additional spectral information, with which the higher-resolution image which can be obtained from the image data of the non-spectrally resolving line detectors 110, 112 can be improved, or with which one or more higher-resolution images, from which particular properties of the product to be examined, for example possibly present foreign bodies made of different materials, can be better recognized can be generated from the image data of the non-spectrally resolving line detectors 110, 112. In particular, the evaluation and control unit 132 or the image processing unit 136 in a device for the X-ray inspection of products according to FIG. 1 can obtain information about the material or the material composition of the irradiated product from the spectral image data of the spectrally resolving line detector 114. Information relating to the thickness of the material or the total thickness of several layers of the same material can also be obtained in this way. How such an evaluation of the image data can be performed is explained further below.

However, the provision of a spectrally resolving line detector has advantages not only in connection with two or more non-spectrally resolving sensors, as has been explained above with reference to the embodiment of an X-ray inspection device according to FIG. 1. Rather, the suitable evaluation of the image data provided by a spectrally resolving line detector also provides advantages when they are combined with image data of a single non-spectrally resolving line detector or when the image data of the single non-spectrally resolving line detector are processed for the purpose of a simple analysis using the information obtained from the image data of the spectrally resolving line detector.

Such embodiments with a single non-spectrally resolving line detector can have a similar structure to the one represented in FIG. 1, wherein only one of the two line detectors 110 and 112 is dispensed with.

Figure 2:
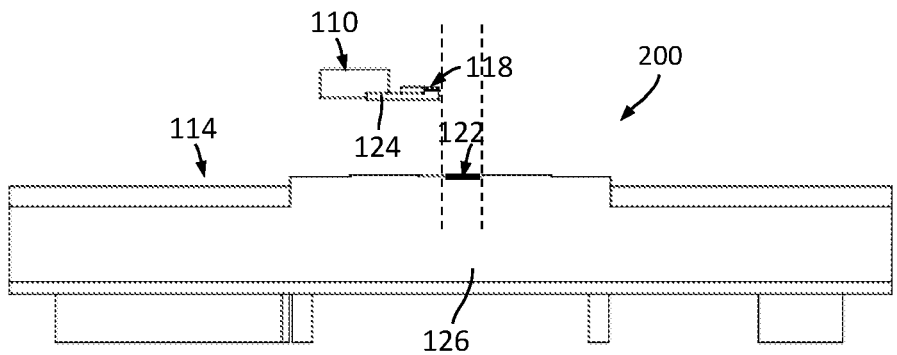
FIG. 2 is a schematic side view of a further embodiment of an X-ray detector device which comprises a combination of a non-spectrally resolving and a spectrally resolving line detector.
Figure 3:
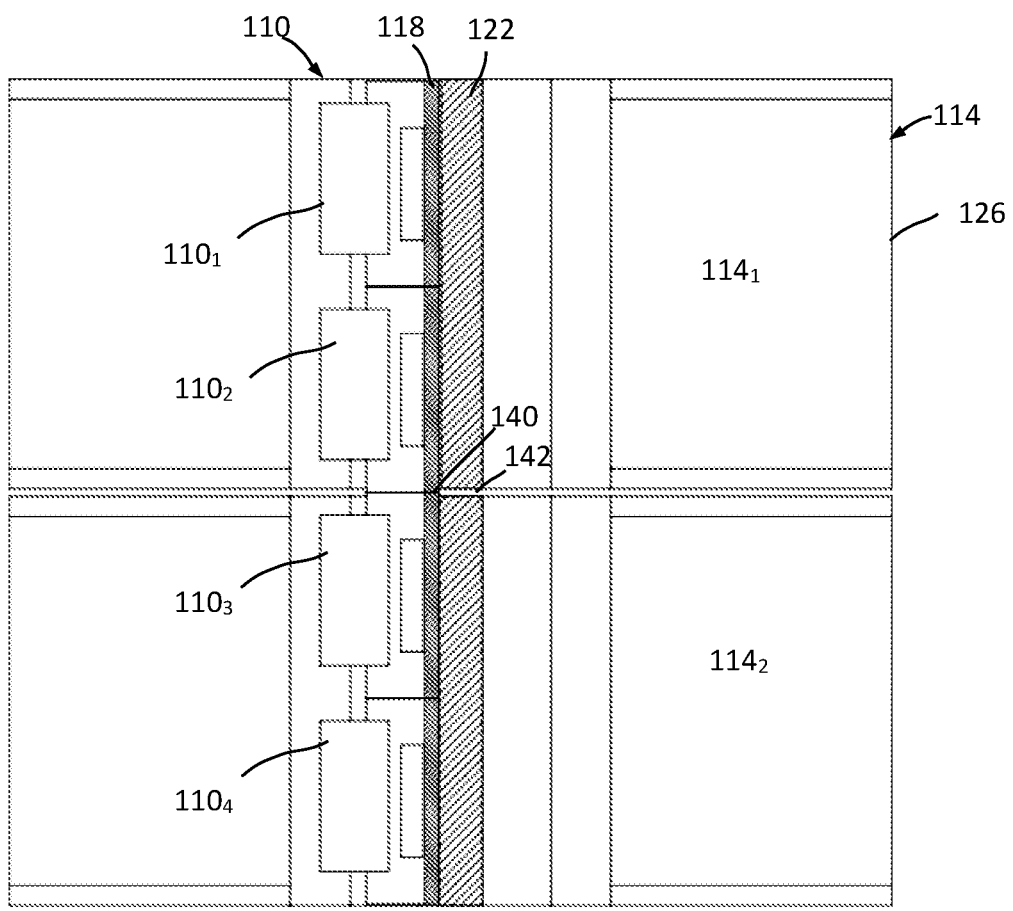
FIG. 3 is a schematic top view of the X-ray detector device shown in FIG. 2.

FIGS. 2 and 3 schematically show the arrangement of a non-spectrally resolving line detector 110 together with a spectrally resolving line detector 114 in the framework of such an X-ray detector device 200. The representation of the remaining components, in particular the housing and the evaluation and control unit, has been omitted. The arrangement of the line detectors 110 and 114, like in the embodiment in FIG. 1, is effected such that the detector lines 118 and 122 have a small distance between them in the horizontal direction and also a small distance between them in the vertical direction (see the side view according to FIG. 2).

From FIG. 3, which represents the two line detectors 110 and 114 in a sectional top view, it can be seen that each of the line detectors 110, 114 is constructed in the form of modules, which are coupled in each case in the direction of the relevant detector line 118, 122. The spectrally resolving line detector 114 consists of modules which have a greater width than the modules of the spectrally resolving line detector 110. Of the modules of the spectrally resolving line detector 114, only two modules, namely the modules $114_1$ and $114_2$, are represented although it will be appreciated that more such modules may be included in a given implementation. These can have, for example, a width (viewed in the direction of the detector line 122) of 10 cm. Of the modules of the non-spectrally resolving line detector 110, modules $110_1$, $110_2$, $110_3$ and $110_4$ are shown although more such modules may be included in a given implementation. These modules have half the width (viewed in the direction of the detector line 118) of the modules of the line detector 114. However, this results in the disadvantage that in the case of every second butt joint 140 of the modules $110_1$, $110_2$, $110_3$ and $110_4$ of the line detector 110 there is also a butt joint 142 of the modules $114_1$ and $114_2$ of the line detector 114. As each detector has an edge region which is not covered by pixels in the immediate vicinity of its side edge, the spatial resolution of the respective line detector is no longer provided at a butt joint. Typically, the edge region of each module, in which pixels are no longer provided, is a width of approximately one to three pixels. Thus, in the case of each line detector 110, 114, at a butt joint information is missing over a width of from two to six pixels in the respective image data.

It is therefore suitable to offset the modules of the line detectors 110, 114 relative to each other such that the butt joints of the modules of one of the line detectors are not present at the butt joints of the modules of the respectively other line detector.

This measure can be seen more clearly in FIG. 4, which represents a section of the detector line 118 of the spectrally resolving line detector 114 and of the detector line 122 of the non-spectrally resolving line detector 114 schematically in a top view. In each case three modules of each line detector 110, 114 are represented, namely modules $110_{i-1}$, $110_i$, and $110_{i+1}$ of line detector 110 and modules $114_{k-1}$, $114_k$, and $114_{k+1}$. The individual pixels, that is, discrete detection locations along the respective detector line 118 and 122, are shown at 118a and 122a, respectively, in FIG. 4. As the modules of the non-spectrally resolving line detector 110 in the embodiment shown are likewise half as wide as the modules of the spectrally resolving line detector 114, through an offset of the modules relative to each other a position at which in each case a butt joint of both line detectors is present at the same time never results. In the embodiments of the line detectors according to FIG. 4, the pixel pitch of the spectrally resolving line detector 114 is twice as large as the pixel pitch of the non-spectrally resolving line detector 110. The edge dimensions of the (square) pixels 118a and 122a of both sensors thus likewise differ approximately by the factor two.

In order to prevent the blind spots of a detector line between two adjacent pixels from coinciding, the line detectors or the relevant modules can also be arranged offset such that in particular at the position of a blind spot between two adjacent larger pixels 122a of the spectrally resolving line detector 114 a blind spot between adjacent pixels 118a of the non-spectrally resolving line detector 110 is not present at the same time. This arrangement is represented in FIG. 5, which shows a section of the detector lines 118, 122 with reference to the schematic, enlarged representation in FIG. 4.

As explained above, the evaluation and control unit 132 can use the image data signals of the line detectors to carry out a monitoring of one of the line detectors (selected line detector) through a comparison with another of the line detectors (reference line detector). This is suitable in particular for monitoring the readiness of the spectrally resolving line detector 114, as such line detectors require a longer start-up time (for example 30 minutes), until usable image data are output. The start-up time can in particular be conditional on the necessary creation of a sufficient charge separation.

For such a comparison, the image data of the reference line detector can be compared, in particular pixel by pixel, with the image data of the selected line detector. The comparison can be effected for example such that the evaluation and control unit 136 knows a target ratio of the signal values provided by comparison pixels corresponding to each other (for example corresponding target ratios for one or more comparison pixel pairs are stored in the evaluation and control unit) and generates a "not-ready signal" if one or more comparison pixel pairs do not achieve the target ratio.

The term "comparison pixel" is introduced in this connection, as the selected line detector and the reference line detector optionally have different pixel sizes or a different pixel pitch (see FIGS. 4 and 5). In particular, the pixels of whichever of these two line detectors has pixels with the larger geometric dimensions can be used as comparison pixels. The respective pixel values can then be used immediately (without further processing) as a value of the comparison pixel of this line detector. If the respectively other line detector has another pixel size, the evaluation and control unit 136 can use all (smaller) pixels of this line detector to ascertain a corresponding value for this comparison pixel which—viewed in the direction of the detector line—lie within the width of the comparison pixel of the line detector with the larger pixel dimensions.

This may be explained in more detail again with reference to FIG. 5 for the monitoring of the spectrally resolving line detector 114 (detector line 122) with the larger pixel dimensions using the non-spectrally resolving line detector 110 (detector line 118) as reference detector for an embodiment according to FIGS. 2 and 3. In each case a pixel 122a in FIG. 5 with its actual dimensions, for example 0.8 mm width, is used as comparison pixel for the spectrally resolving line detector 114. This width covers the shaded regions of three pixels 118a of the non-spectrally resolving line detector 110 which together form the comparison pixel of the line detector 110. To generate the target ratio, the evaluation and control unit 136 generates the ratio of the pixel values which the line detector 114 provides for the relevant pixel (or comparison pixel), and the proportionate pixel values which the line detector 110 provides for the three actual pixels 118a which form the corresponding comparison pixel of the line detector 110. The completely covered actual pixel 118a (represented entirely shaded) with its unaltered pixel value is taken into account, and the two outer actual pixels 118a of the line detector 110 only partially covered by the comparison pixel 122a of the line detector 114 with the proportionate pixel value with which the relevant pixel (viewed in the direction of the detector line) lies within the width of the comparison pixel of the line detector 114.

This procedure is carried out pixel by pixel for each comparison pixel of the line detector 114 to be monitored and the corresponding comparison pixel of the reference line detector 110.

Instead of choosing the actual pixels with the larger geometric dimension as comparison pixels, however, any desired other width of a detector line or the actual pixels covered by this width can also be chosen as comparison pixels.

If it is established in the case of such a monitoring that the line detector to be monitored does not provide correct results, thus the device 100 for the X-ray inspection of products or the X-ray detector device 108 generates a "not-ready signal", then a superordinate control unit (not represented) to which the "not-ready signal" is fed and which is designed to control a total processing system comprising the device 100 can stop the processing system and/or generate an alarm signal.

However, the superordinate control unit can also be designed such that, despite the presence of a "not-ready signal", the system continues to be operated, wherein the evaluation and control unit 136 of the X-ray inspection device 100 in such an emergency operating mode continues to work such that only the correctly working line detector(s) are actuated and/or the relevant image data signals are used for an evaluation. Such an emergency operation can be maintained for example until a particular product batch has been completed.

In this emergency operating mode the evaluation and control unit 136 can also provide further measures, for example a specific actuation of the at least one X-ray source 106. Thus, to increase the detector accuracy of the remaining line detector(s), in particular to improve the signal-to-noise ratio, for example the power of the X-ray source 106 can be increased. The sometimes present redundancy of spectrally resolving line detectors and non-spectrally resolving line detectors can thus be utilized in an emergency operating mode in order to continue to operate the X-ray inspection device 100, but then with reduced capacities. However, if these capacities or properties are sufficient to guarantee a sufficient inspection of the products to be examined, depending on the application case, then the emergency operating mode represents a considerable advantage.

In the following it is explained what items of information the spectrally resolving sensor 114 can provide which lead to an improved recognition accuracy in a processing of the image data of the non-spectrally resolving sensors 110, 112 with higher spatial resolution.

Figure 6:
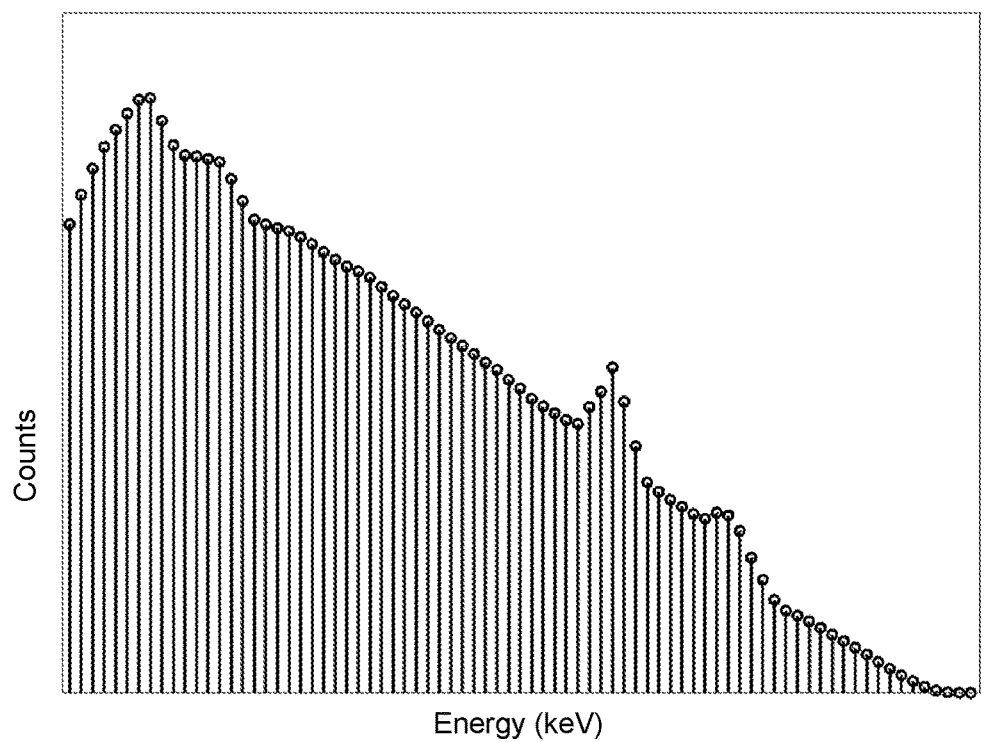
FIG. 6 is an example of an energy spectrum which was generated by a pixel of a spectrally resolving line detector.

FIG. 6 shows by way of example the image data which are provided by the spectrally resolving line detector 114 for a particular pixel. Here, the entire captured energy range, for example from 20 keV to 80 keV, is divided into a particular number of energy channels, wherein each energy channel has a particular (usually constant) spectral width, which results from the width of the entire captured spectral range divided by the number of energy channels, for example 128 or 256 energy channels. The line detector 114 provides one spectral value, which is denoted by "counts" in FIG. 6 because such a spectrally resolving line detector as a rule counts individual photons, for each energy channel and assigns the recorded photons, depending on their energy, to a particular energy channel. The progression represented in FIG. 6 corresponds to a typical light image which is generated by the line detector 114 without the presence of a product in the beam path of the X-ray beam 116.

The spectral values are transmitted with the image data signal to the evaluation and control unit 136 as image data. The evaluation and control unit 136 can evaluate these image data in different ways in order to obtain information, in order to use these image data either for an improved evaluation of the image data of the non-spectrally resolving line detectors 110, 112, or in order to combine the image data of the spectrally resolving line detector 114 with the image data of the non-spectrally resolving line detectors 110, 112 to form a total image which, optionally using further information which is obtained from the image data of the non-spectrally resolving line detector 114, makes an improved image evaluation possible.

The capacity of a spectral resolution of the line detector 114 can be utilized in order to obtain partial image data for the generation of a dual energy image. For this purpose, the evaluation and control unit 136 can perform any desired weighting of the spectral values pixel by pixel. Such a weighting can be effected in that a factor, which is multiplied by the respective spectral value, is assigned to each individual energy channel. A severe restriction of the spectrum can also be achieved hereby, if the factor zero is assigned to selected energy channels.

Figure 7:
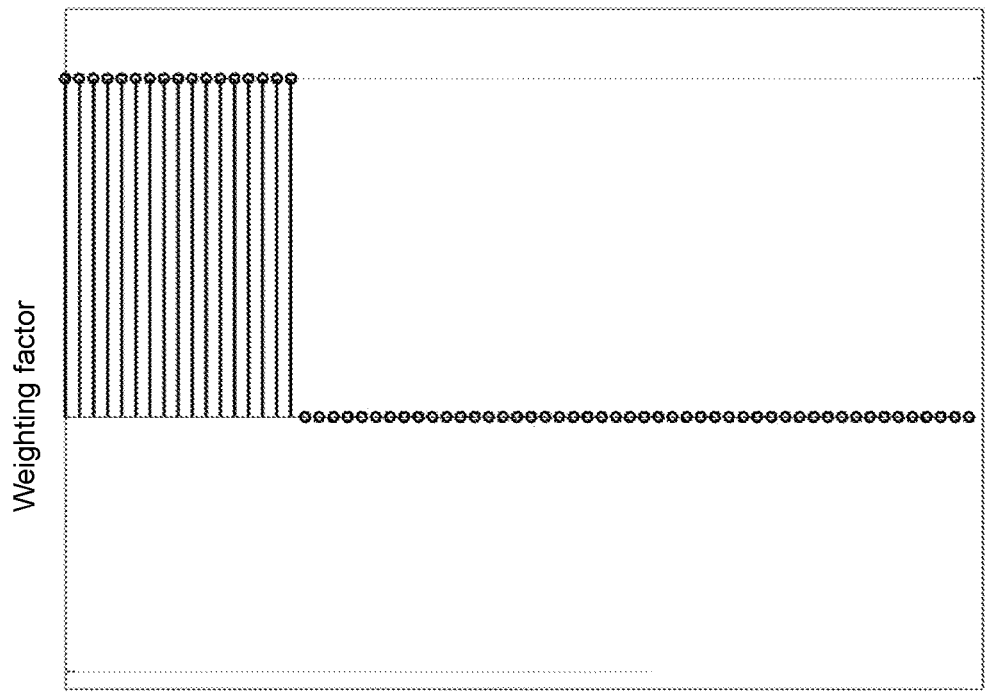
FIG. 7 is a weighting profile for weighting the energy channels of an energy spectrum according to FIG. 6.

FIG. 7 shows a weighting profile which has a separate weighting factor for each energy channel. This profile provides a constant weighting, for example with the factor one, for a number of energy channels in the lower region of the entire spectrum. All other energy channels are weighted with the factor zero. The thus-weighted spectral values can be added together to generate a total spectral value. The total spectral values can then be used as partial image data for the generation of a dual energy image, wherein a non-spectrally resolving line detector, for example the line detector 110 in the embodiment according to FIGS. 2 and 3, can provide further partial image data for the generation of the dual energy image. The evaluation and control unit 136 combines the grayscale image data, which the non-spectrally resolving line detector 110 provides, with the partial image data of the spectrally resolving line detector 114 to form the desired dual energy image, wherein the evaluation and control unit 136 weights the respective partial image data pixel by pixel for this purpose. For the image data provided by the spectrally resolving line detector 114, this weighting can already be effected in the framework of the weighting of the energy channels.

This procedure provides the advantage that, unlike in the case of a non-spectrally resolving line detector, the energy channels which are selected to form the partial image data for a dual energy image can be weighted not only with a constant factor, but with a variable factor.

As already explained above, the spectrally resolving line detector 114 can also be designed such that it preselects which energy channels are transmitted to the evaluation and control unit 136 as part of an image data signal. For example, the line detector 114 can be adjusted manually or by the evaluation and control unit 136 such that it emits only particular energy channels as an image data signal. The line detector 114 can also be designed such that it emits the selected energy channels already integrated, i.e. it adds up the spectral values of the selected energy channels.

In this case, a less complex processing of the image data of the line detector 114 results for the evaluation and control unit 136.

The non-spectrally resolving line detector 114 thus makes it possible to generate a dual energy image using a flexible spectrum. This can be established through the simple evaluation of the image data signal of the line detector 114, or the line detector 114 is actuated such that it already provides corresponding spectrally restricted image data or even total spectral values (see above).

In this way, a variable dual energy image can be generated by means of a single non-spectrally resolving line detector 110, but which has a high spatial resolution, and a spectrally resolving line detector 114, which nevertheless has only a relatively low spatial resolution. The spectrum of the spectrally resolving line detector 114 can be varied such that particular features of a product to be examined can be better recognized in the dual energy image, for example with a higher contrast.

The evaluation of the image data of the two line detectors 110, 114 obtained by means of a single scan can also be effected such that several partial evaluations are carried out. For example, different dual energy images can be generated using differently weighted image data of the spectrally resolving line detector 114. For example, the spectrum of the image data of the line detector 114 in an evaluation can be chosen (for example through a corresponding weighting) such that foreign bodies made of a particular material, for example steel, can be recognized with high contrast. In a further evaluation, the spectrum of the image data of the line detector 114 can be chosen differently, for example in order to generate a dual energy image in which foreign bodies made of a different material, for example polyethylene, are to be recognized with high contrast.

In addition to the generation of partial image data for a dual energy image, the one or more spectrally resolving line detectors provide still further advantages. In particular, the evaluation of a dual energy image generated in this way or the evaluation of a dual energy image which has been created using exclusively image data which were generated by means of non-spectrally resolving sensors can be improved. These are improvements which take effect at the level of the image evaluation, i.e. in the analysis of an already generated total image (such a total image is always a grayscale image).

The spectral resolution which such a line detector provides makes it possible, applying suitable evaluation methods, to obtain information as to the material or materials of which the product to be examined consists. However, this information can be determined pixel by pixel only with the lower spatial resolution of the spectrally resolving line detector. Furthermore, it is possible, from the image data of the at least one spectrally resolving line detector, to obtain information about the thickness of one or more material layers of which the product to be examined consists.

Information as to the material or materials of which the product to be examined consists can be obtained through different methods for evaluating the spectral data which the spectrally resolving line detector provides. For example, it is possible to ascertain, through the irradiation of a product which consists of a known material or a known material combination, the spectral progression of the attenuation which the product causes. For this purpose, a light image can be detected first, i.e. the spectral progression of the X-radiation $I_0(E_k, x_i)$ ($I_0$ denotes the radiation intensity detected without product; $E_k$ denotes the energy of the X-ray quanta in the energy channel k; $x_i$ denotes the location in the line detector, in particular the pixel no. i) if no product is irradiated. The measurement result $I(E_k, x_i)$ (I denotes the radiation intensity detected with product) in the case of irradiation of a product thus, together with the light image, provides in each case the attenuation $D(E_k, x_i)$ caused by the absorption in the product, wherein the attenuation results from the Beer-Lambert law:

$$D(E_k,x_i)=\ln\ [I(E_k,x_i)/I_0(E_k,x_i)]=\mu(E_k)\cdot d_i \qquad \text{eq. (1)}$$

wherein $d_i$ denotes the thickness of the product in the beam path of the proportion of radiation which is detected by the pixel $x_i$, and $\mu(E_k)$ denotes the absorption coefficient of the material in the beam path. In the case of a material combination with an at least approximately constant composition inside the beam path, an average absorption coefficient for the relevant material combination can be used. As the thickness $d_i$ only represents a constant factor (per pixel), a characteristic progression of absorption behavior $\ln(I/I_0)$ independent of the thickness results, which can be determined using the detected spectrum (i.e. the spectral values per pixel) and a previously detected spectrum of a light image. This spectral progression can be known to the evaluation and control unit for a product to be examined without foreign bodies (also called "good product" in the following), i.e. corresponding information can be stored in the evaluation and control unit or the latter can have access to corresponding externally available information.

Thus, the evaluation and control unit, through a comparison of the measured spectral intensities (measurement of the light image and measurement of the product) with one or more known spectral intensity progressions for each pixel, can establish whether a known material is contained in the relevant beam path of the product. If, for example, yogurt or cheese is to be examined as product, the evaluation and control unit can confirm for each pixel of the spectrally resolving line detector whether the spectral progression matches that of the expected product. If the measured spectral progression deviates from the known progression by more than an admissible deviation, a conclusion can already be drawn using the image data of the spectrally resolving sensor that a foreign body is contained in partial volumes of the product corresponding to the respective pixel.

However, if it can be confirmed that no inadmissible deviations from the characteristic spectral progression to be expected are present on the relevant pixel, it can be assumed that there is a good product in the respective beam path. As the absorption coefficient $\mu(E_k)$ of the relevant material is likewise known and can be stored in or at least made available to the evaluation and control unit, the relevant thickness of the product or length of the beam path through the product (based on the respective pixel $x_i$) can be calculated.

With this information, the evaluation and control unit can perform the evaluation of a grayscale image which was generated for example by means of the dual energy method explained above, using a dynamic threshold value which is used to recognize foreign bodies.

In the X-ray inspection of products to discover foreign bodies, i.e. any type of undesired components or elements to be detected of a product to be examined, it is usual to use a static threshold value. If, for example, a foreign body has a higher absorption than the material surrounding it of the product to be examined, the static threshold value will be placed in a region which, on the one hand, generates as small as possible a probability of a false alarm and, on the other hand, makes a sufficiently reliable recognition of foreign bodies possible. For example, for this purpose, an average grayscale value, which is multiplied by a previously known factor to ascertain the static threshold value, can be ascertained from the total image of the product.

As the grayscale image to be analyzed in the case of a product with unknown variations in the thickness or in a case where several products, for example cuts of meat, can overlap each other can have larger regions with clearly different brightness or a clearly different grayscale value (the absorption of the X-radiation through the product is dependent on the material thickness), the use of such a static threshold value leads to problems. However, if it is known, as a result of the information which the spectrally resolving line detector provides, that only "admissible" material is present even in the darker regions, then the evaluation and control unit can assume that at least the larger darker regions do not represent foreign bodies, but that they are thickness variations of the product or overlapping product regions. For the analysis of these regions the evaluation and control unit can thus establish a threshold value of their own in each case. This dynamic threshold value can vary from region to region of the grayscale image to be analyzed. The probability of a false alarm can thus be reduced.

The combination of at least one non-spectrally resolving line detector with a higher spatial resolution and at least one spectrally resolving line detector with lower spatial resolution can thus be used in order to achieve an advantageous generation of a total image, in particular a dual energy image or multiple energy image, from the respective image data and/or in order to make an advantageous evaluation of a dual energy image or multiple energy image generated in such a way or a dual energy image or multiple energy image generated in a manner known per se through the use of image data from non-spectrally resolving line detectors possible.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

LIST OF REFERENCE CHARACTERS

100 X-ray inspection device
102 product
104 radiation-generating device
106 X-ray source
108 X-ray detector device
110 non-spectrally resolving line detector 110₁ module
110₂ module
110₃ module
110₄ module
110_{i-1} module
110_i module
110_{i+1} module
112 non-spectrally resolving line detector
114 spectrally resolving line detector
114₁ module
114₂ module
114_{k-1} module
114k module
114_{k+1} module
116 fan-shaped X-ray beam
118 pixel line
118a individual pixel
120 pixel line
122 pixel line
112a individual pixel
124 carrier
126 carrier
128 housing
130 opening
132 evaluation and control unit
134 data capture unit
136 image processing unit
138 X-ray filter
140 butt joint (modules of line detector 110)
142 butt joint (modules of line detector 114)
200 X-ray detector device
B relative movement direction
E center plane of X-ray beam

The invention claimed is:

1. An X-ray detector device for a device for the X-ray inspection of products, the X-ray detector device including:
   (a) a first line detector with a first discrete spatial resolution, the first line detector being operable to detect X-radiation at discrete locations along a first capture line extending along a capture width transverse to a movement direction of relative movement between a product being examined and the X-ray detector device, the detection by the first line detector being non-spectrally resolved so as to generate first image data including one grayscale value for each discrete location along the first capture line;
   (b) a second line detector with a second discrete spatial resolution less than or equal to the first discrete spatial resolution, the second line detector being operable to detect X-radiation at discrete locations along a second capture line extending along the capture width parallel to the first capture line, the detection by the second line detector being spectrally resolved so as to generate second image data including for each discrete location along the second capture line a number of channel values where each channel value represents the X-ray quanta detected within a different respective energy range; and
   (c) an evaluation and control unit connected to receive the first image data and second image data or data derived from the first image data and data derived from the second image data, the evaluation and control unit being operable to combine information from the first image data with information from the second image data to detect, with at least the first discrete spatial resolution, a feature of the product being examined.

2. The device of claim 1 wherein the feature of the product being examined comprises one of position of a foreign body inside the product, size of the foreign body, material of the foreign body, thickness of the product, material of the product, thickness of material layers of the product, and position of overlap regions of elements of the product.

3. The device of claim 1 wherein the first line detector and second line detector are housed within a common housing.

4. The device of claim 1 wherein the evaluation and control unit is operable to actuate the first line detector and second line detector such that a synchronous capture of the first image data and second image data is effected depending on the speed of the relative movement between the product being examined and the X-ray detector device, so that the first image data and the second image data correspond substantially to a single beam path through the product being examined.

5. The device of claim 1 wherein the evaluation and control unit is operable to actuate the first line detector and the second line detector such that an asynchronous capture of the first image data and second image data is effected wherein the first line detector operates at a first line-scanning rate which is greater than a pixel pitch of the first line detector divided by the movement speed of the product being examined and wherein the second line detector operates at a second line-scanning rate which is greater than a pixel pitch of the second line detector divided by the movement speed of the product being examined.

6. The device of claim 1 wherein the evaluation and control unit is operable to apply interpolation or geometric transformation to the first image data and second image data each captured at different points along the length of the product being examined to create a total image from such first image data and second image data.

7. The device of claim 1 wherein:
   (a) the first line detector includes two or more first detector modules arranged together along the first capture line with a respective first detector butt joint formed between adjacent first detector modules;
   (a) the second line detector includes two or more second detector modules arranged together along the second capture line with a respective second detector butt joint formed between adjacent second detector modules; and
   (c) the first detector butt joints and the second detector butt joints are offset relative to each other in the direction of the first capture line.

8. The device according to claim 1 wherein:
   (a) a total spectral value for each discrete location along the second capture line is created by one of (i) weighting all channel values of the respective discrete location along the second capture line and adding such weighted channel values together, or (ii) weighting some but not all channel values of the respective discrete location along the second capture line and adding such weighted channel values together, or (iii) adding some but not all of the channel values of the respective discrete location and weighting the result of such addition; and
   (b) the evaluation and control unit is operable to generate multiple energy image data from the first image data and the total spectral value for each discrete location along the second capture line.

9. The device of claim 8 wherein channel value weightings suitable for detection of one or more particular features of the product being examined are accessible by the evaluation and control unit.

10. The device of claim 8 wherein the evaluation and control unit is operable to perform a first evaluation with the first image data and the second image data employing a first weighting for the channel values to produce first multiple energy image data from the second image data, and is further operable to perform a second evaluation with the first image data and the second image data employing a second weighting for the channel values to produce second multiple energy image data from the second image data.

11. The device of claim 1 wherein:
   (a) the evaluation and control unit is operable to evaluate the second image data to identify product regions with different layer thicknesses or regions of overlapping products; and
   (b) for an inspection of the identified regions, the evaluation and control unit is operable to employ a threshold value which is set depending on the grayscale values of one or more of the identified regions.

12. The device of claim 1 wherein the evaluation and control unit is operable to compare the image data of a selected one of the first line detector and second line detector to the image data of the non-selected one of the first line detector and second line detector and to generate a "not ready signal" where the comparison shows a deviation above a defined limit.

13. The device of claim 12 wherein the comparison is performed between corresponding discrete locations comprising comparison pixels selected from the image data of the respective line detector such that the corresponding comparison pixels cover a corresponding width on the respective capture line, and wherein where a respective one of the comparison pixels does not lie with its entire width within the width of the corresponding comparison pixel, the respective one of the comparison pixels is weighted with the ratio with which that pixel lies with its width within the width of the corresponding comparison pixel.

14. A device for the X-ray inspection of products, the device including:
   (a) a radiation-generating device with at least one X-ray source for generating X-radiation with a selected spectral width, wherein the X-radiation is transmitted in a transmission direction through a product moving in a movement direction and movement speed relative to the X-radiation;
   (b) a first line detector with a first discrete spatial resolution, the first line detector being operable to detect X-radiation at discrete locations along a first capture line extending along a capture width transverse to a movement direction of relative movement between a product being examined and the first line detector, the detection by the first line detector being non-spectrally resolved so as to generate first image data including one grayscale value for each discrete location along the first capture line;
   (c) a second line detector with a second discrete spatial resolution less than or equal to the first discrete spatial resolution, the second line detector being operable to detect X-radiation at discrete locations along a second capture line extending along the capture width parallel to the first capture line, the detection by the second line detector being spectrally resolved so as to generate second image data including for each discrete location along the second capture line a number of channel values where each channel value represents the X-ray quanta detected within a different respective energy range; and
   (d) an evaluation and control unit connected to receive the first image data and second image data or data derived from the first image data and data derived from the second image data, the evaluation and control unit being operable to combine information from the first image data with information from the second image data to detect, with at least the first discrete spatial resolution, a feature of the product being examined.

15. The device of claim 14 wherein the second capture line lies outside of a shadow of the first line detector with respect to the X-ray source and the first capture line lies outside of a shadow of the second line detector with respect to the X-ray source and wherein the first and second capture lines have a minimal spacing in the movement direction of the product being examined.

16. The device of claim 15 wherein the first line detector and the second line detector, viewed in the transmission direction, are arranged overlapping, wherein the first and second capture lines have a different distance from the at least one X-ray source, and wherein the first and second capture lines have a minimal spacing in the transmission direction.

* * * * *